(12) United States Patent
Weisshaupt

(10) Patent No.: US 9,572,579 B2
(45) Date of Patent: Feb. 21, 2017

(54) SURGICAL CLIP

(71) Applicant: Aesculap AG, Tuttlingen (DE)

(72) Inventor: Dieter Weisshaupt, Immendingen (DE)

(73) Assignee: Aesculap AG, Tuttlingen (DE)

( * ) Notice: Subject to any disclaimer, the term of this patent is extended or adjusted under 35 U.S.C. 154(b) by 706 days.

(21) Appl. No.: 13/777,169

(22) Filed: Feb. 26, 2013

(65) Prior Publication Data

US 2013/0172914 A1  Jul. 4, 2013

Related U.S. Application Data

(63) Continuation of application No. PCT/EP2011/063488, filed on Aug. 4, 2011.

(30) Foreign Application Priority Data

Oct. 4, 2010  (DE) .................. 10 2010 037 949

(51) Int. Cl.
*A61B 17/08* (2006.01)
*A61B 17/122* (2006.01)
(Continued)

(52) U.S. Cl.
CPC ......... *A61B 17/083* (2013.01); *A61B 17/1227* (2013.01); *B29C 45/73* (2013.01); *A61B 17/1285* (2013.01); *A61B 2017/00004* (2013.01); *A61B 2017/00526* (2013.01); *A61B 2017/00862* (2013.01); *B29C 2045/7343* (2013.01); *B29L 2031/7546* (2013.01)

(58) Field of Classification Search
CPC ............ A61B 17/122–17/1285; A61B 17/083; B29C 45/73; B29C 45/76; B29C 45/78; B29C 45/0017; B29C 2045/7343; B29C 2045/735; B29C 2045/002; B29C 2045/0022; B29C 2045/14762
USPC .......................................... 606/151, 157–158
See application file for complete search history.

(56) References Cited

U.S. PATENT DOCUMENTS

| 482,232 A | 9/1892 | Delaney |
|---|---|---|
| 884,256 A | 4/1908 | Addie |

(Continued)

FOREIGN PATENT DOCUMENTS

| DE | 26 47 018 | 5/1977 |
|---|---|---|
| DE | 26 58 478 | 4/1978 |

(Continued)

*Primary Examiner* — Gregory Anderson
*Assistant Examiner* — Erich Herbermann
(74) *Attorney, Agent, or Firm* — Lipsitz & McAllister, LLC

(57) ABSTRACT

A surgical clip is provided, having two clip arms and a resiliently flexible element pivotally connecting the two clip arms together. The two clip arms each have a first free end, which are held in parallel to and in contact with each other with a predetermined closing force by the flexible element in a rest position. At a second end opposite the free end, the clip arms are held connected to a wall section of the flexible element that is arranged substantially transverse to the longitudinal direction of the clip arms, extends between the second ends of the clip arms and has a first wall portion facing towards the clip arms and a second wall portion facing away from the clip arms. The flexible element is made from a plastics material by injection molding. The first wall portion is produced with a greater shrinkage than the second wall portion.

11 Claims, 3 Drawing Sheets

(51) Int. Cl.
*B29C 45/73* (2006.01)
*A61B 17/128* (2006.01)
*A61B 17/00* (2006.01)
*B29L 31/00* (2006.01)

(56) References Cited

U.S. PATENT DOCUMENTS

| | | | |
|---|---|---|---|
| 1,589,076 A | 6/1926 | Haskins | |
| 1,758,490 A | 5/1930 | Aderer | |
| 1,837,277 A | 12/1931 | Lund | |
| 3,598,125 A | 8/1971 | Cogley | |
| 3,802,437 A | 4/1974 | Kees, Jr. | |
| 3,805,792 A | 4/1974 | Cogley | |
| 3,827,438 A | 8/1974 | Kees, Jr. | |
| 4,192,315 A | 3/1980 | Hilzinger et al. | |
| 4,324,248 A | 4/1982 | Perlin | |
| 4,360,023 A | 11/1982 | Sugita et al. | |
| 4,416,266 A * | 11/1983 | Baucom | 606/158 |
| 4,444,187 A | 4/1984 | Perlin | |
| 4,484,581 A | 11/1984 | Martin et al. | |
| 4,602,631 A | 7/1986 | Funatsu | |
| 4,765,335 A | 8/1988 | Schmidt et al. | |
| 4,777,950 A | 10/1988 | Kees, Jr. | |
| 4,796,625 A | 1/1989 | Kees, Jr. | |
| 4,899,134 A * | 2/1990 | Wheeless, Jr. | A61B 17/12 340/539.1 |
| 4,932,955 A | 6/1990 | Merz et al. | |
| 4,943,298 A | 7/1990 | Fujita et al. | |
| 4,961,743 A | 10/1990 | Kees, Jr. et al. | |
| 4,966,603 A | 10/1990 | Focelle et al. | |
| 4,971,055 A | 11/1990 | von Zeppelin | |
| 4,983,176 A * | 1/1991 | Cushman et al. | 606/151 |
| 5,074,870 A | 12/1991 | von Zeppelin | |
| 5,207,692 A * | 5/1993 | Kraus | A61B 17/083 227/901 |
| 5,312,426 A | 5/1994 | Segawa et al. | |
| 5,361,463 A | 11/1994 | Revis | |
| 5,474,569 A | 12/1995 | Zinreich et al. | |
| 5,474,732 A * | 12/1995 | Korthoff et al. | 264/230 |
| 5,520,701 A | 5/1996 | Lerch | |
| 5,676,676 A * | 10/1997 | Porter | A61B 17/128 606/151 |
| 5,695,505 A * | 12/1997 | Yoon | A61B 17/0487 606/151 |
| 5,924,176 A | 7/1999 | Lee | |
| 5,938,666 A * | 8/1999 | Reynolds | A61B 17/122 606/120 |
| 5,944,729 A | 8/1999 | Blake | |
| 6,179,850 B1 | 1/2001 | Goradia | |
| 6,210,418 B1 * | 4/2001 | Storz et al. | 606/142 |
| 6,251,117 B1 | 6/2001 | Kringel et al. | |
| 6,457,218 B1 * | 10/2002 | Lawrence | 24/563 |
| 6,537,277 B2 | 3/2003 | Vom Berg et al. | |
| 6,776,783 B1 | 8/2004 | Frantzen et al. | |
| 2002/0022844 A1 | 2/2002 | Vom Berg et al. | |
| 2002/0111643 A1 * | 8/2002 | Herrmann et al. | 606/158 |
| 2002/0117869 A1 | 8/2002 | Wang et al. | |
| 2008/0004637 A1 * | 1/2008 | Klassen | A61B 17/122 606/142 |
| 2009/0240266 A1 | 9/2009 | Dennis | |
| 2013/0184726 A1 | 7/2013 | Weisshaupt et al. | |
| 2014/0114332 A1 * | 4/2014 | Lutze | 606/151 |

FOREIGN PATENT DOCUMENTS

| | | | |
|---|---|---|---|
| DE | 29 52 618 | 7/1981 | |
| DE | 31 39 488 | 4/1983 | |
| DE | 34 19 928 | 4/1985 | |
| DE | 35 23 031 | 1/1986 | |
| DE | 37 22 311 | 1/1989 | |
| DE | 89 11 948 | 1/1990 | |
| DE | 43 19 829 | 8/1994 | |
| DE | 296 04 518 | 6/1996 | |
| DE | 690 28 200 | 2/1997 | |
| DE | 37 23 167 | 4/1997 | |
| DE | 297 08 218 | 8/1997 | |
| DE | 19737976 | 3/1999 | |
| DE | 198 09 121 | 8/1999 | |
| DE | 40 00 086 | 5/2000 | |
| DE | 199 07 354 | 9/2000 | |
| DE | 10 2006 031 092 | 1/2008 | |
| EP | 0 346 084 | 12/1989 | |
| EP | 1 196 094 | 1/2003 | |
| GB | 1 557 682 | 12/1979 | |
| GB | 2 161 206 | 1/1986 | |
| WO | WO 99/44511 | 9/1999 | |
| WO | WO 2010096174 A1 * | 8/2010 | A61B 1/00087 |

* cited by examiner

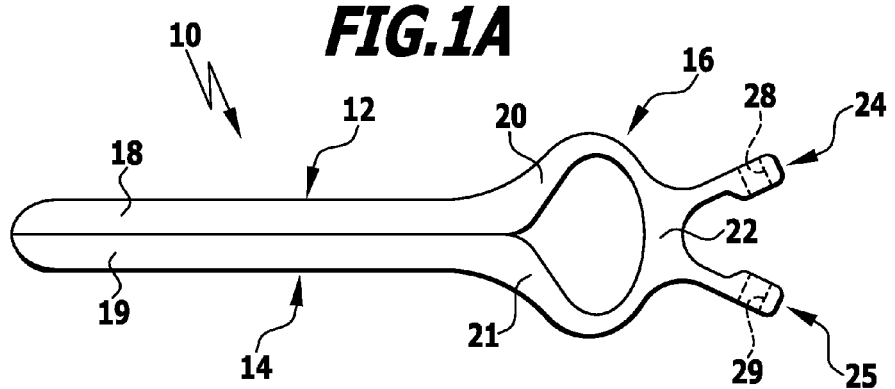
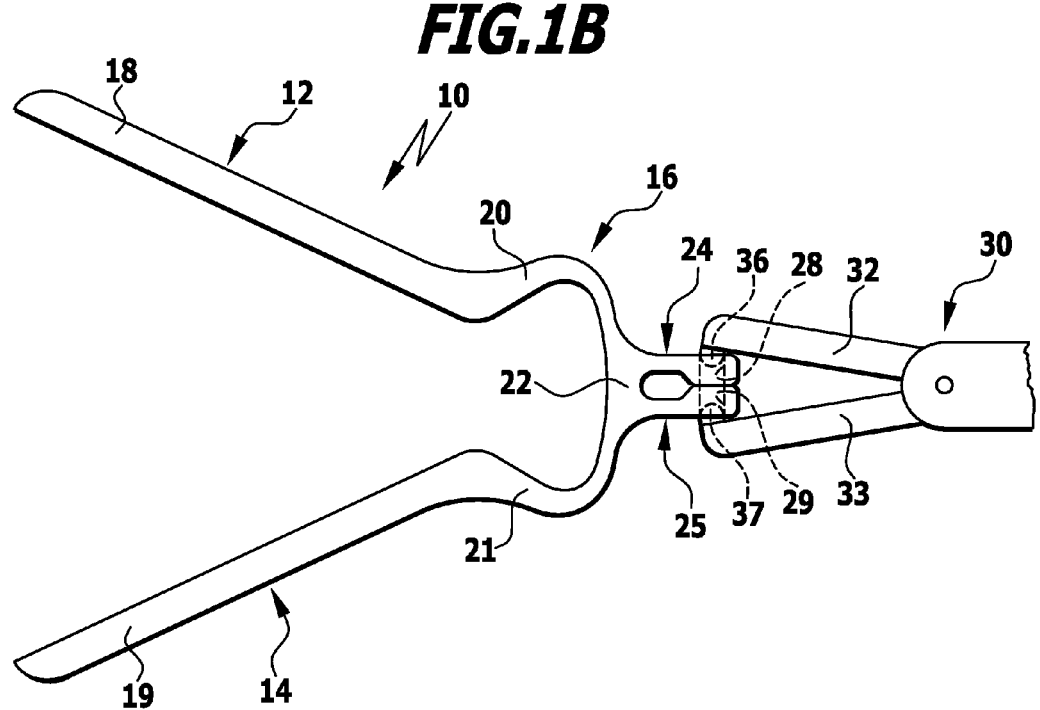

FIG.3
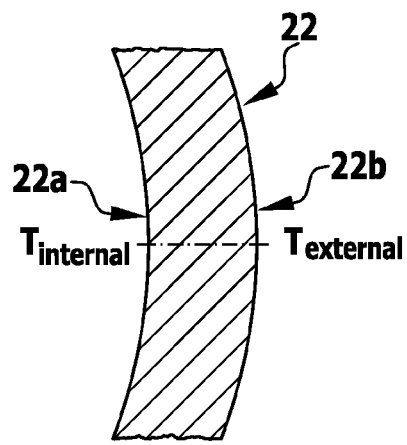
$T_{internal} > T_{external}$
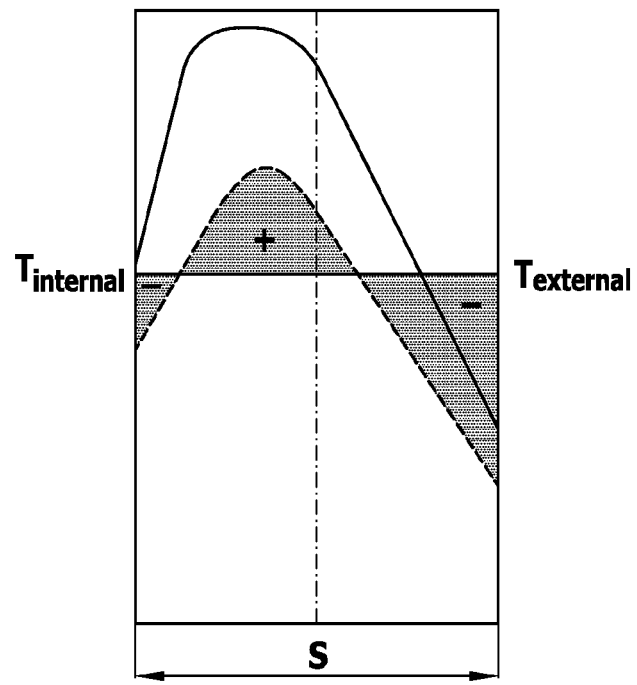
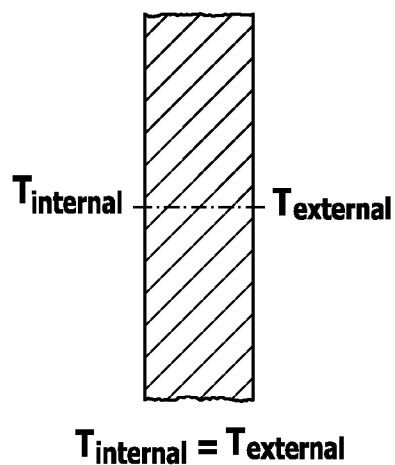
$T_{internal} = T_{external}$
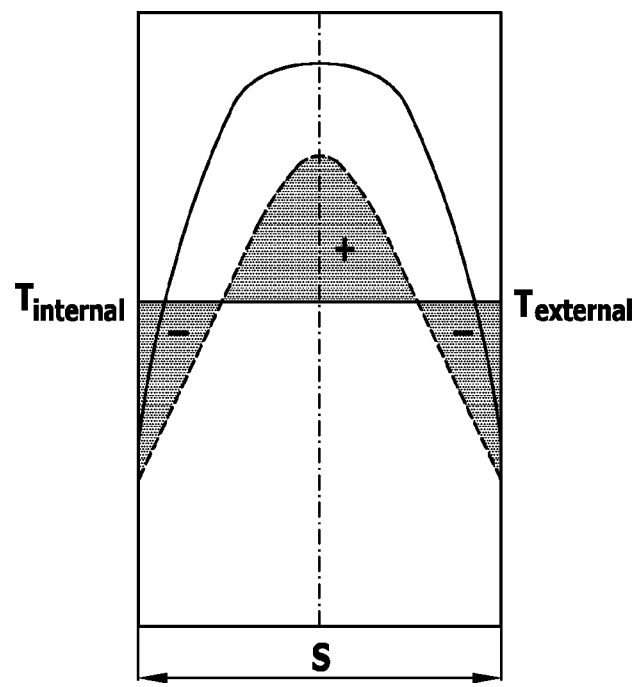

SURGICAL CLIP

This application is a continuation of international application number PCT/EP2011/063488 filed on Aug. 4, 2011 and claims the benefit of German application number 10 2010 037 949.2 filed on Oct. 4, 2010, which are incorporated herein by reference in their entirety and for all purposes.

BACKGROUND OF THE INVENTION

The invention relates to a surgical clip, in particular for use as an implant, wherein use as a cerebral aneurysm clip has outstanding importance here.

Surgical clips are known that have two clip arms and a resiliently flexible element which connects the two clip arms to each other at one of their ends.

The two clip arms each have a first free end, these first free ends being held parallel to and in contact with each other with a predetermined closing force by the resiliently flexible element when the clip is in a rest position, while a second end opposite the respective free end is held on the resiliently flexible element.

An essential parameter of the surgical clips of the kind mentioned at the outset is their closing force: it must be precisely set and also, in particular if the surgical clip is used as an implant, be maintained on a permanent basis.

The production of the surgical clips of the kind mentioned at the outset is therefore an elaborate process.

It is an object of the invention to provide a surgical clip that can be produced more easily and in particular also more cost-effectively.

SUMMARY OF THE INVENTION

In accordance with the invention, this object is accomplished by a surgical clip having the features of claim 1.

The present invention makes use of an effect that is generally observed as undesirable in the injection moulding process in order to injection-mould the resiliently flexible element of the clip with a predetermined closing force, wherein by specifically using different cooling rates for the first and second wall portions, greater shrinkage is produced in the first wall portion than in the second wall portion.

Different rates of cooling in injection-moulded plastic parts give rise to the effect of warpage in the finished part when removed from the injection mould. The present invention specifically uses this effect in order to produce, via the greater shrinkage in the first wall portion, "warpage" of the resiliently flexible element or the wall section thereof after removal from the injection mould, based on which the bias exerted by the resiliently flexible element and thus the predetermined closing force of the clip can be adjusted.

In the clip constructed in accordance with the invention, provision may be made for the clip arms to be produced from a metallic material and the resiliently flexible element to be integrally formed on the clip arms by injection moulding, for example.

The clip arms can then be positioned in the tool so as to be already in direct contact with each other, and the resiliently flexible element or the wall section thereof is integrally formed on the second ends of the clip arms during the injection moulding process.

Alternatively, the clip arms are likewise produced from a plastics material, in which case they are preferably produced by injection-moulding them in one piece with the resiliently flexible element. It is understood that in the latter case, the two clip arms cannot be injection-moulded with their free ends in contact with each other but are separated from each other by a wall of the injection mould and are typically kept parallel to and spaced apart from each other.

The injection moulding technique in accordance with the invention nevertheless allows a one-piece clip to be produced which, in unstressed condition, after removal from the injection mould, has clip arms that are parallel to and in contact with each other and exhibits a predetermined closing force.

Said clip constructed in accordance with the invention then additionally has the advantage that when the clip is closed, the two clip arms come into contact with each other with their tips first, and the further contact until the clip arms as a whole are parallel to and in contact with each other develops from the tips of the clip arms to the ends thereof adjacent to the resiliently flexible element.

It is thereby possible to prevent tissue that is to be captured by the clip from being pushed outward.

The plastics that lend themselves to the manufacture of the resiliently flexible element and also the clip arms insofar as they are likewise made of a plastics material are to be selected with a view to their use as implants. In this connection, particularly suitable plastics are high-temperature plastics, such as polyimides or polyketones, in particular polyetherketones, more preferably polyetheretherketone (PEEK).

Resorbable plastics can also be taken into consideration when selecting the plastics; in using these, the clip is resorbed over time and does not remain inside the patient's body as a foreign body.

The differential shrinkage between the first wall portion and the second wall portion in the wall section of the resiliently flexible element can in particular be implemented within the scope of a variotherm injection moulding technique, wherein by specific cooling or specific heating or a combination of both the corresponding temperature profiles can be provided in the tool when producing the first and second wall portions of the wall section.

In a more preferred embodiment of the present invention, provision is made for the resiliently flexible element to have on the side thereof facing away from the clip arms, in particular connecting to the second wall portion, stop elements which form a stop when the clip is transferred from the rest position to an application position in which the free ends of the clip arms are spaced apart from each other.

This prevents the surgical clip, when applied to a vessel by the tool typically provided therefor, from deforming in an inadmissible manner which would have a negative effect on the closing force, in particular the permanent closing force, of the clip.

In handling the surgical clips, care must therefore be taken that they experience deformation only in the range where plastic deformation of the resiliently flexible element does not yet occur so that upon return towards the rest position of the clip arms, the full predetermined closing force of the clip becomes and remains effective.

A maximum opening angle of the clip arms in the application position of up to approximately 45° is advantageous for a large number of surgical clips.

More preferably, the stop elements can be configured to be of complementary form, thus allowing mutual centering of the stop elements to be achieved, associated with correct orientation of the clip arms relative to each other in the opened application position.

Preferably, the complementary-shaped stop elements can be configured such that lateral and/or axial guiding of the stop elements results when the clip arms are transferred to the application position.

The wall section of the resiliently flexible element having the first wall portion, which is produced with a higher shrinkage than the second wall portion, preferably will have a substantially hollow-cylindrical contour. Said wall section can also be a segment or part of an oval cross-section.

In a more preferred embodiment of the invention, provision is made for the stop elements to have on their surfaces facing away from each other positioning elements for a tool so that the surgical clip can be gripped with an applying tool in a predetermined mutual positioning.

Said positioning elements can also serve to establish a secure connection between the applicator and the surgical clip and thus prevent accidental loss of the clip from the tool during the application procedure.

Said positioning elements are in particular provided in the form of depressions, in particular also bores, in the stop elements.

The surgical clip is in particular configured as an aneurysm clip, in particular also as a cerebral aneurysm clip.

The invention further relates to a method for producing a surgical clip as described above, wherein an injection moulding tool is used which allows different temperature controls in the wall of the injection moulding tool adjacent to the first and second wall portions so that the first wall portion of the resiliently flexible element of the clip can be produced with a higher shrinkage.

These and further advantages of the invention are described in more detail below with reference to the drawings.

BRIEF DESCRIPTION OF THE DRAWINGS

FIGS. 1A and 1B show a surgical clip in accordance with the invention in a rest position and in an application position, respectively;

FIG. 3 is a diagrammatic view of a wall section of the surgical clip.

DETAILED DESCRIPTION OF THE INVENTION

Figure 2:
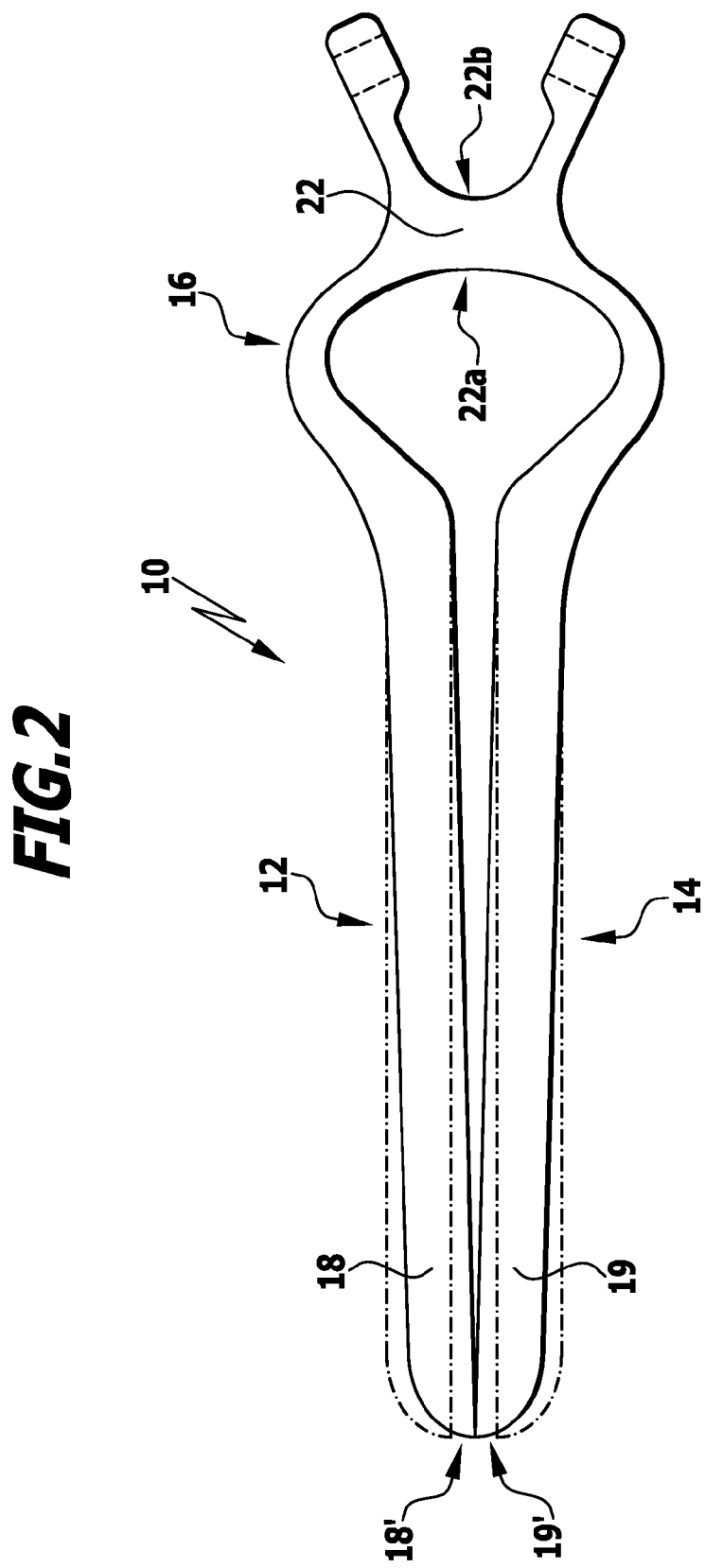
FIG. 2 shows the surgical clip of FIG. 1A with different opening angles.

FIG. 1A shows a surgical clip 10 constructed in accordance with the invention having a first clip arm 12, a second clip arm 14 arranged parallel thereto and a resiliently flexible element 16 which connects the two clip arms to each other.

The clip arms 12 and 14 have free ends 18, 19 which are parallel to and in contact with each other, whereas the second ends 20, 21 lying opposite the first free ends 18, 19 are integrally connected to the spring element 16 or the wall section 22 thereof.

The spring element 16 has on its side facing away from the clip arms 12, 14 stop elements 24, 25 which project perpendicularly from the wall section 22 and form between them an angle of approximately 45°.

The stop elements 24, 25 have bores 28, 29 formed in their free ends remote from the wall section 22 which serve as positioning aids for an applicator tool, as will be shown and described in the following with reference to FIG. 1B.

FIG. 1B depicts the clip 10 in an application position in which the clip 10 is gripped at the stop elements 24, 25 thereof by a clip applicator 30 via the latter's gripping tools 32, 33.

The gripping tools 32, 33 force the two stop elements 24, 25 into direct contact with each other, whereupon the clip arms 12, 14 open at an angle of approximately 45° (application position). The stop elements 24, 25 ensure that the clip 10, in particular the wall section 22 of the resiliently flexible element 16, is not deformed beyond the admissible range so that the deformation is performed well within the elastic range and plastic deformation of the resiliently flexible element 16 cannot occur.

In order to facilitate gripping the clip 10 and make the contact between the applicator tool 30 and the clip 10 more secure, the gripping tools 32, 33 are provided with cylindrical projections 36, 37 which can engage in the bores 28, 29 of the stop elements 24, 25, thus establishing and ensuring a secure connection between the clip 10 and the applicator 30.

FIG. 2 schematizes the clip 10 constructed in accordance with the invention in two different positions, wherein the representation of the clip arms 12, 14 shown in dashed-and-dotted lines indicates the mutual position thereof within the injection moulding tool.

When the clip 10 constructed in accordance with the invention is removed from the injection moulding tool, initially the free ends 18, 19 of the two clip arms 12, 14 approximate each other, with a first contact of the clip arms 12, 14 being established at the extreme ends thereof facing away from the resiliently flexible element 16, i.e., at the tips 18', 19'. Subsequently, as a result of the differential shrinkage effect existing in the wall section 22 on the side of a first wall portion 22a as against a second wall portion 22b, complete closing of the free ends 18, 19 of the clip arms 12, 14 onto each other is achieved so that they are in full surface contact with each other (rest position), as shown in FIG. 1A.

The effect of achieving differential shrinkage between the first and second wall portions of the wall section 22 is shown schematically in FIG. 3.

In accordance with the invention, the temperature during cooling of the injection moulding material within the tool in the region of the wall section 22 of the resiliently flexible element 16 is controlled such that the temperature of the second wall portion 22b is lower than the temperature on the side of the first wall portion 22a so that greater shrinkage is attained on the side of the first wall portion 22a. When the surgical clip 10 constructed in accordance with the invention is demoulded from the injection mould, this then results in a bias corresponding to a predetermined closing force.

The bias of the resiliently flexible element and thus the closing force of the clip 10 can be adjusted by choice of the internal and external temperatures, or the differential shrinkage, in the first and second wall portions.

The precise choice of the temperatures depends on the one hand on the thickness S of the wall section 22 as well as on the desired closing force and finally also on the type of plastics material being processed.

At the bottom of FIG. 3 is shown, for comparison only, how an injection moulded part behaves when the temperatures T internal and T external are kept the same during cooling of the plastics material within the injection mould with otherwise identical parameters.

No differential shrinkage is produced between the inner and outer parts; therefore, the stresses U occurring in the wall section are balanced, and the wall section itself exhibits no warpage or cannot generate bias.

The invention claimed is:

1. Surgical clip for use as an implant, comprising: two clip arms, and a resiliently flexible element via which the two clip arms are pivotally connected to each other, the two clip arms each having a first free distal end, the first free distal ends being held in parallel to and in contact with each other with a predetermined closing force by the resiliently flexible element when the clip is in a rest position, each of the clip arms at a corresponding second proximal end thereof opposite the first free distal end being held connected to a wall section of the resiliently flexible element, the wall section being arranged substantially transverse to a longitudinal direction of the clip arms, extending between the second proximal ends of the clip arms, and having a first wall portion facing towards the clip arms and a second wall portion facing away from the clip arms, wherein: the resiliently flexible element is made of a plastics material by injection molding, the plastics material comprises a polyetherketone, the first wall portion of the wall section is produced with a greater shrinkage than the second wall portion, the two clip arms comprise elongated clip arms, and the elongated clip arms come into contact with each other with the free distal ends first during transfer from an application position to the rest position, and come into full surface-to-surface contact with each other when in the rest position, the resiliently flexible element has on a side thereof facing away from the clip arms stop elements which form a stop when the clip is transferred from the rest position to the application position in which the free distal ends of the clip arms are spaced apart from each other.

2. Surgical clip in accordance with claim 1, wherein the clip arms are made of a metallic material and the resiliently flexible element is integrally formed on the clip arms by injection molding.

3. Surgical clip in accordance with claim 1, wherein the clip arms are made of a plastics material and are formed by injection-molding them in one piece with the resiliently flexible element.

4. Surgical clip in accordance with claim 1, wherein an opening angle of the clip arms in the application position is limited to a value of approximately 45°.

5. Surgical clip in accordance with claim 1, wherein the stop elements are configured to be of complementary form.

6. Surgical clip in accordance with claim 5, wherein the complementary-configured stop elements are configured such that at least one of a lateral and an axial guiding of the stop elements results when the clip arms are transferred to the application position.

7. Surgical clip in accordance with claim 1, wherein the wall section of the resiliently flexible element has a substantially hollow-cylindrical contour.

8. Surgical clip in accordance with claim 1, wherein the stop elements have on exterior surfaces thereof positioning elements for a tool.

9. Surgical clip in accordance with claim 1, wherein the clip is configured as an aneurysm clip.

10. Surgical clip in accordance with claim 1, wherein:
the plastics material of the resiliently flexible element comprises a PEEK material, and
the clip arms are made of a plastics material comprising one of a polymide or a polyetherketone.

11. Method for producing a surgical clip, wherein the surgical clip comprises: two clip arms, and a resiliently flexible element via which the two clip arms are pivotally connected to each other, the two clip arms each having a first free distal end, the first free distal ends being held in parallel to and in contact with each other with a predetermined closing force by the resiliently flexible element when the clip is in a rest position, each of the clip arms at a corresponding second proximal end thereof opposite the first free distal end being held connected to a wall section of the resiliently flexible element the wall section being arranged substantially transverse to a longitudinal direction of the clip arms, extending between the second proximal ends of the clip arms, and having a first wall portion facing towards the clip arms and a second wall portion facing away from the clip arms, wherein: the plastics material comprises a polyetherketone, the two clip arms comprise elongated clip arms, and the elongated clip arms come into contact with each other with the free distal ends first during transfer from an application position to the rest position, and come into full surface-to-surface contact with each other when in the rest position, the method comprising: in the process of manufacturing the resiliently flexible element of the clip, a molten liquid plastics material is fed into a mold in an injection molding process and cooled, and as the plastics material cools, the mold is held in a region thereof forming the wall section of the resiliently flexible element at a higher temperature on a side of the first wall portion than on a side of the second wall portion to produce the first wall portion with a greater shrinkage than the second wall portion, wherein the resiliently flexible element has on a side thereof facing away from the clip arms stop elements which form a stop when the clip is transferred from the rest position to the application position in which the free distal ends of the clip arms are spaced apart from each other.

\* \* \* \* \*